US007429602B2

United States Patent
Trach et al.

(10) Patent No.: US 7,429,602 B2
(45) Date of Patent: *Sep. 30, 2008

(54) TREATING CONJUNCTIVITIS BY TOPICALLY ADMINISTERING AN EPINASTINE SOLUTION TO THE CONJUNCTIVA

(75) Inventors: Volker Trach, Biberach (DE); Gerold Duschler, Ehingen (DE)

(73) Assignee: Boehringer Ingelheim Pharma GmbH & Co. Kg, Ingelheim (DE)

( * ) Notice: Subject to any disclaimer, the term of this patent is extended or adjusted under 35 U.S.C. 154(b) by 23 days.

This patent is subject to a terminal disclaimer.

(21) Appl. No.: 11/863,008

(22) Filed: Sep. 27, 2007

(65) Prior Publication Data

US 2008/0009476 A1    Jan. 10, 2008

Related U.S. Application Data

(63) Continuation of application No. 10/271,180, filed on Oct. 15, 2002, which is a continuation of application No. 09/706,650, filed on Nov. 6, 2000, now abandoned.

(60) Provisional application No. 60/167,771, filed on Nov. 29, 1999.

(30) Foreign Application Priority Data

Nov. 12, 1999 (DE) ................. 199 54 516

(51) Int. Cl.
*A61K 31/445* (2006.01)
(52) U.S. Cl. .................. 514/319; 514/322; 514/912
(58) Field of Classification Search .................. None
See application file for complete search history.

(56) References Cited

U.S. PATENT DOCUMENTS

| | | | |
|---|---|---|---|
| 4,313,931 A | | 2/1982 | Walther et al. |
| 5,668,133 A | | 9/1997 | Yanni et al. |
| 5,942,503 A | | 8/1999 | Jung et al. |
| 6,649,602 B1 | | 11/2003 | Yanni |
| 2002/0037297 A1 | | 3/2002 | Crespo |
| 2003/0050303 A1 | | 3/2003 | Trach |
| 2005/0288274 A1 | | 12/2005 | Trach |
| 2007/0185082 A1 | | 8/2007 | Trach |
| 2007/0197503 A1 | | 8/2007 | Trach |

*Primary Examiner*—Zohreh A Fay
(74) *Attorney, Agent, or Firm*—Michael P. Morris; Mary-Ellen M. Devlin; Timothy X. Witkowski

(57) ABSTRACT

Treating allergic conjunctivitis by administered aqueous solutions containing epinastine, optionally in the form of its racemate or its enantiomers and optionally, in the form of the pharmacologically acceptable acid addition salts thereof, to the conjunctiva.

4 Claims, No Drawings

TREATING CONJUNCTIVITIS BY TOPICALLY ADMINISTERING AN EPINASTINE SOLUTION TO THE CONJUNCTIVA

RELATED APPLICATIONS

This application is a continuation of U.S. Ser. No. 10/271,180, filed Oct. 15, 2002, which is a continuation of U.S. Ser. No. 09/706,650, filed Nov. 6, 2000, now abandoned, which claims priority to German Application No. 199 54 516.2, filed Nov. 12, 1999, and claims benefit of U.S. Provisional Application Ser. No. 60/167,771, filed on Nov. 29, 1999, each of which is hereby incorporated by reference.

FIELD OF THE INVENTION

The invention relates to topically administered aqueous solutions containing epinastine, optionally in the form of its racemates, its enantiomers, and optionally in the form of the is pharmacologically acceptable acid addition salts thereof.

BACKGROUND OF THE INVENTION

Allergic reactions of the eye (hereinafter referred to as ocular allergic reactions) signifies a series of differently defined syndromes. The following are examples of ocular allergic reactions, e.g., seasonal allergic conjunctivitis, perennial allergic conjunctivitis, giant cell conjunctivitis, vernal keratoconjunctivitis, or atopic keratoconjunctivitis. Examples of allergic reactions of the nose (hereinafter referred to as nasal allergic reactions) include seasonal allergic rhinitis and perennial allergic rhinitis, for example.

The immunological mechanism on which ocular and nasal allergic reactions are based comprises, inter alia, inflammatory processes caused by histamine. The allergic reactions produced by the release of histamine occur at an early stage of the ocular and nasal allergic reactions mentioned above. Moreover, ocular and nasal allergic reactions may be due to the release of other mast cell mediators as well as toxic eosinophilic granule proteins and enzymes. The influx of neutrophils and eosinophils into the tissue of the ocular conjunctiva and the nasal mucous membrane leads to a late phase reaction, hereinafter referred to as LPR. LPR normally occurs within a period of 3-6 hours after the initial histamine-mediated allergic reaction. LPR is also characterized by the occurrence of vasodilation and chemosis and by the swelling of the conjunctiva and the nasal mucous membrane.

Whereas histamine-produced allergic reactions can be counteracted by administering antihistamines, the influx of neutrophils and eosinophils into the tissue of the ocular conjunctiva and the nasal mucous membrane remains unaffected by administering pure antihistamines.

Problem of the Invention

The problem of the present invention is therefore to provide topically administrable solutions which inhibit the influx of neutrophils and tosinophils into the tissue of the ocular conjunctiva and the nasal mucous membrane; thereby reducing or preventing the occurrence of LPR and are therefore characterized by a longer lasting duration of activity.

DETAILED DESCRIPTION OF THE INVENTION

It has been found, surprisingly, that topically administrable aqueous solutions containing epinastine, optionally in the form of its racemate, its enantiomers and possibly in the form of the pharmacologically acceptable acid addition salts thereof, may be used to solve the problem on which the invention is based, since they inhibit the influx of neutrophils and eosinophils into the tissue of the ocular conjunctiva and nasal mucous membrane, thereby reducing or preventing the occurrence of LPR and are accordingly characterized by a longer lasting duration of activity.

The compound epinastine (3-amino-9,13b-dihydro-1H-dibenz-[c,f]imidazol[1,5-a]azepine) and the acid addition salts thereof were described for the first time in German Patent Application P 30 08 944.2.

The effect of the topically administered solutions containing epinastine as inhibitors of the influx of eosinophils and neutrophils was demonstrated using the so-called passive ocular anaphylaxis model in rats.

Description of Experiment 72 hours after the rats have been sensitized by injecting antiserum into the eyelids of the test animals, a fresh provocation was induced in them by intravenous administration of ovalbumin. Some of the experimental animals were pretreated by the administration of solution containing epinastine according to the invention into the conjunctival sac 15 minutes before the ovalbumin is administered. Two hours after the administration of ovalbumin the experimental animals were killed and the conjunctiva was investigated for its content of eosinophils and neutrophils and the mast cell granulation was determined.

Results

The animals pretreated with epinastine solution according to the invention (0.05-0.5%) had a significantly lower content of eosinophils in their conjunctiva. The animals pretreated with epinastine solution according to the invention had a significantly lower content of lymphocytes in their conjunctiva ($p<0.01$). In the animals pretreated with epinastine solution according to the invention, a roughly 35% inhibition of mast cell degranulation was determined ($p<0.01$).

Consequently, the invention relates to topically administered aqueous solutions containing epinastine, optionally in the form of its racemate, its enantiomers and optionally in the form of the pharmacologically acceptable addition salts thereof, in a concentration of 0.005 to 0.5, preferably 0.02 to 0.1, most preferably 0.03 to 0.07 mg/ml of solution.

The abovementioned topically administered aqueous solutions containing epinastine hydrochloride are preferred according to the invention.

Suitable aqueous solvents are physiologically acceptable aqueous solvents, physiologically acceptable saline solutions being particularly preferred.

According to the invention, topically administered solutions are preferably prepared which typically contain 0.005 to 0.5, preferably 0.02 to 0.1, most preferably 0.03 to 0.07 mg/ml of epinastine, optionally in the form of its racemate, its enantiomers and optionally in the form of the pharmacologically acceptable acid addition salts thereof, as well as physiological saline solutions as the main carriers. The pH of the solutions according to the invention should preferably be maintained within the range from 6.5 to 7.2 by means of a suitable buffer system. The preparations may also contain conventional, pharmaceutically acceptable excipients, preservatives, stabilizers, and/or penetration promoters.

The preferred carrier which may be used in the solutions according to the invention is purified water and preferably a physiological saline solution.

Without restricting the subject matter of the invention to the following, the excipients which may be used according to the invention include viscosity agents such as polyvinyl alcohol, povidone, hydroxypropylmethylcellulose, poloxamers, carboxymethylcellulose, carbomers, and hydroxyethylcellulose.

Without restricting the subject matter of the invention to the following, the preferred preservatives which may be used in the solutions according to the invention include benzalkonium chloride, chlorobutanol, thimerosal, phenyl mercury acetate, and phenyl mercury nitrate.

The penetration promoters may be, for example, surfactants, specific organic solvents such as dimethylsulfoxide and other sulfoxides, dimethylacetamide and pyrrolidone, specific amides of heterocyclic amines, glycols such as propylene glycol, propylene carbonate, oleic acid, alkylamines and derivatives thereof, various cationic, anionic, non-ionogenic, and amphoteric surfactants and the like.

The present invention also relates to the use of epinastine, optionally in the form of its racemate, its enantiomers and optionally in the form of the pharmacologically acceptable acid addition salts thereof, for producing the topically administered aqueous solutions according to the invention for treating disorders of the ocular conjunctiva or the nasal mucous membranes in which there is therapeutic value in inhibiting the influx of neutrophils and eosinophils into the tissue of the ocular conjunctiva or the nasal mucous membrane in allergic reactions.

The abovementioned use for inhibiting LPR is preferred, whilst it is particularly preferable to use the preparation to treat the diseases listed at the beginning.

The Examples shown in Table 1 illustrate the invention without restricting it.

TABLE 1

|  | Solution 1 0.05% [g/100 ml] | Solution 2 0.01% [g/100 ml] | Solution 3 0.05% [g/100 ml] | Solution 4 0.10% [g/100 ml] | Solution 5 0.01% [g/100 ml] | Solution 6 0.05% [g/100 ml] | Solution 7 0.10% [g/100 ml] |
| --- | --- | --- | --- | --- | --- | --- | --- |
| Epinastine hydrochloride | 0.0500 | 0.0100 | 0.0500 | 0.1000 | 0.0100 | 0.0500 | 0.1000 |
| Na-EDTA | 0.0500 | 0.0500 | 0.0500 | 0.0500 | — | — | — |
| Sodium chloride | 0.5000 | 0.5000 | 0.5000 | 0.5000 | 0.5000 | 0.5000 | 0.5000 |
| Sodium dihydrogen phosphate dihydrate | 0.7800 | 0.7800 | 0.7800 | 0.7800 | 0.4100 | 0.4100 | 0.4100 |
| Benzalkonium chloride | 0.0101 | 0.0101 | 0.0101 | 0.0101 | 0.0101 | 0.0101 | 0.0101 |
| Sodium hydroxide | 0.0001 | 0.0001 | 0.0001 | 0.0001 | — | — | — |
| Sodium dihydrogen phosphate dihydrate | — | — | — | — | 0.6500 | 0.6500 | 0.6500 |
| Hydroxyethylcellulose | — | — | — | — | 0.1000 | 0.1000 | 0.1000 |
| Water | 99.4198 | 99.4598 | 99.4198 | 99.3698 | 99.0749 | 99.0349 | 99.9849 |
|  | 100.8100 | 100.8100 | 100.8100 | 100.8100 | 100.7550 | 100.7550 | 100.7550 |

Substances may be added as necessary or as desired in order to adjust the tonicity of the solution. Such substances include salts and especially sodium chloride, potassium chloride, mannitol, and glycerol or other suitable physiologically acceptable agents for adjusting tonicity, without restricting the invention to the above.

Various buffers and substances may be used to adjust the pH, provided that the preparation obtained is physiologically acceptable. These buffers might include acetate buffer, citrate buffer, phosphate buffer and borate buffer.

Similarly, physiologically acceptable antioxidants which may be used according to the invention include sodium metabisulphite, sodium thiosulphate, acetylcysteine, butylated hydroxyanisole, and butylated hydroxytoluene, without restricting the invention to this list.

Other carrier components which may be incorporated in the solutions according to the invention are chelating agents. The preferred chelating agent is disodium edetate (Na-EDTA), although other chelating agents may also be used instead of or in conjunction with disodium edetate.

The abovementioned topically administered aqueous solutions according to the invention may be applied either to the conjunctiva or to the nasal mucous membrane. Solutions for ophthalmic use are of equal importance to solutions for nasal application for the purposes of the present invention.

The invention relates not only to the solutions according to the invention mentioned hereinbefore but also to the use of the abovementioned topically administered aqueous solutions for inhibiting the influx of neutrophils and eosinophils into the tissue of the ocular conjunctiva or the tissue of the nasal mucous membrane.

We claim:

1. A method for treating allergic conjunctivitis, comprising topically administering to the conjunctiva of a host in need of such treatment a solution comprising:
   (a) a pharmaceutically active ingredient consisting essentially of epinastine, optionally in the form of its racemate, or an enantiomer thereof, or a pharmacologically acceptable acid addition salt thereof, in a concentration of 0.005 to 0.5 mg/ml of solution;
   (b) water or physiologically acceptable saline; and
   (c) a preservative,
   optionally also including one or more chelating agents, viscosity agents, penetration promoters, antioxidants, substances to adjust the tonicity of the solution, or a physiologically acceptable buffer.

2. A method for inhibiting the influx of neutrophils and eosinophils into the tissue of the ocular conjunctiva of a host to reduce the occurrence of late phase allergic reactions, comprising:
   topically administering to the ocular conjunctiva of the host a solution comprising:
   (a) a pharmaceutically active ingredient consisting essentially of epinastine, optionally in the form of its racemate, an enantiomer thereof, or a pharmacologically acceptable acid addition salt thereof, in a concentration of 0.005 to 0.5 mg/ml of solution;
   (b) water or physiologically acceptable saline; and
   (c) a preservative,
   optionally also including one or more chelating agents, viscosity agents, penetration promoters, antioxidants, substances to adjust the tonicity of the solution or a physiologically acceptable buffer.

3. The method of claim 1, wherein the solution comprises:
(a) a pharmaceutically active ingredient consisting essentially of epinastine hydrochloride, in a concentration of about 0.5 mg/ml of solution;
(b) water or physiologically acceptable saline;
(c) benzalkonium chloride as a preservative; and
(d) a buffer to adjust the pH within the range of 6.5 to 7.2.

4. The method of claim 2, wherein the solution comprises:
(a) a pharmaceutically active ingredient consisting essentially of epinastine hydrochloride, in a concentration of about 0.5 mg/ml of solution;
(b) water or physiologically acceptable saline;
(c) benzalkonium chloride as a preservative; and
(d) a buffer to adjust the pH within the range of 6.5 to 7.2.

* * * * *